US00PP37325P2

(12) United States Plant Patent
Ammerlaan

(10) Patent No.: US PP37,325 P2
(45) Date of Patent: Mar. 10, 2026

(54) ***ECHEVERIA* PLANT NAMED 'OVPEARLS15'**

(50) Latin Name: ***Echeveria agavoides* Lem**
Varietal Denomination: OVPEARLS15

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 18/831,529

(22) Filed: Mar. 28, 2025

(30) Foreign Application Priority Data

Nov. 21, 2024 (NL) ..... 2024/2735

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan Mccormick Ewoldt
*Assistant Examiner* — Zachariah Allan Kay
(74) *Attorney, Agent, or Firm* — Samuel R. McCoy, Jr.

(57) ABSTRACT

A new and distinct variety of *Echeveria* plant named 'OVPEARLS15' which is characterized by a flattened globular profile with an abundance of glossy, upturned, narrow obovate foliage arranged in a compact basal rosette, yellow-green juvenile foliage with a greyed-orange mucronate laminar tip, which matures to a darker green foliage with a greyed-red laminar tip. The new variety has shown to be uniform and stable in the resulting generations from asexual propagation.

4 Drawing Sheets

Latin name of the genus and species: The Latin name of the genus and species of the novel variety disclosed herein is *Echeveria agavoides* Lem.

Variety denomination: The inventive variety of *Echeveria* disclosed herein has been given the variety denomination 'OVPEARLS15'.

CROSS REFERENCE TO RELATED APPLICATIONS

This application claims priority to the Community Plant Variety Rights application number 2024/2735, filed Nov. 21, 2024, which is herein incorporated by reference.

BACKGROUND OF THE INVENTION

Parentage: 'OVPEARLS15' is a spontaneous whole plant mutation found growing amongst a cultivated population of the parent plant, an unnamed *Echeveria agavoides* plant (unpatented), at a commercial greenhouse in Bleiswijk, the Netherlands in 2015. The plant was observed to exhibit unique foliage and growth characteristics when compared to the parent plant and all other progenies. After confirming the stability of the unique characteristics first observed, the new plant was selected for commercialization and given the name, 'OVPEARLS15'.

Asexual Reproduction: Asexual reproduction of the new cultivar 'OVPEARLS15', by way of rooting leaf cuttings, was first initiated in 2016 at the inventor's commercial greenhouse in Bleiswijk, the Netherlands. Through several subsequent generations, the unique features of this cultivar have proven to be stable and true to type.

SUMMARY OF THE INVENTION

The cultivar 'OVPEARLS15' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS15'. These characteristics in combination distinguish 'OVPEARLS15' as a new and distinct *Echeveria* cultivar:

1. 'OVPEARLS15' exhibits an abundance of glossy succulent foliage with a concave and upwardly curved aspect, arranged in a compact rosette; and
2. 'OVPEARLS15' exhibits oblong to narrow obovate foliage with an abruptly acute to broad apiculate apex and a mucronate tip; and
3. 'OVPEARLS15' exhibits yellow-green juvenile foliage with a greyed-orange laminar tip that darkens as the plant matures into darker green foliage with a greyed-purple laminar tip; and
4. 'OVPEARLS15' exhibits foliage with entire, smooth margins that are colored greyed-green and tinged with greyed-orange to greyed-red towards the laminar apices.

BOTANICAL DESCRIPTION OF THE PLANT

Figure 1:
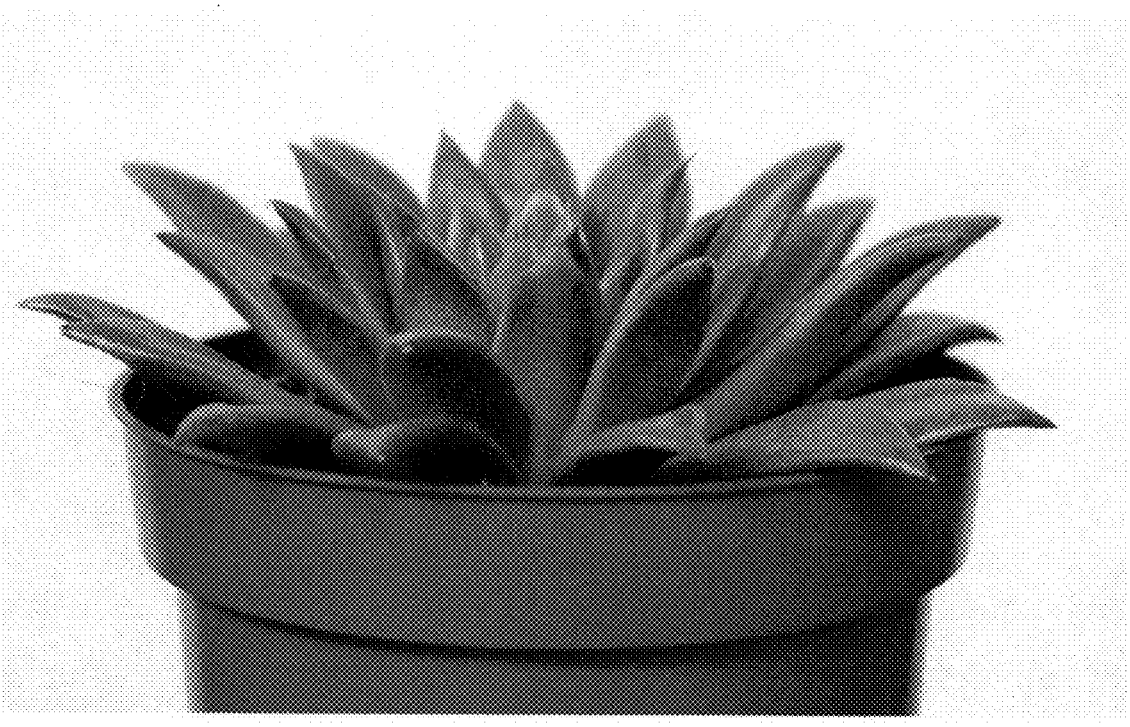
FIG. 1 illustrates, as nearly true as it is reasonably possible to make the same in color photographs of this type, an exemplary plant of 'OVPEARLS15' grown in a commercial greenhouse in Bleiswijk, the Netherlands. This plant is approximately 1 year old, shown planted in a 13 cm container.
Figure 2:
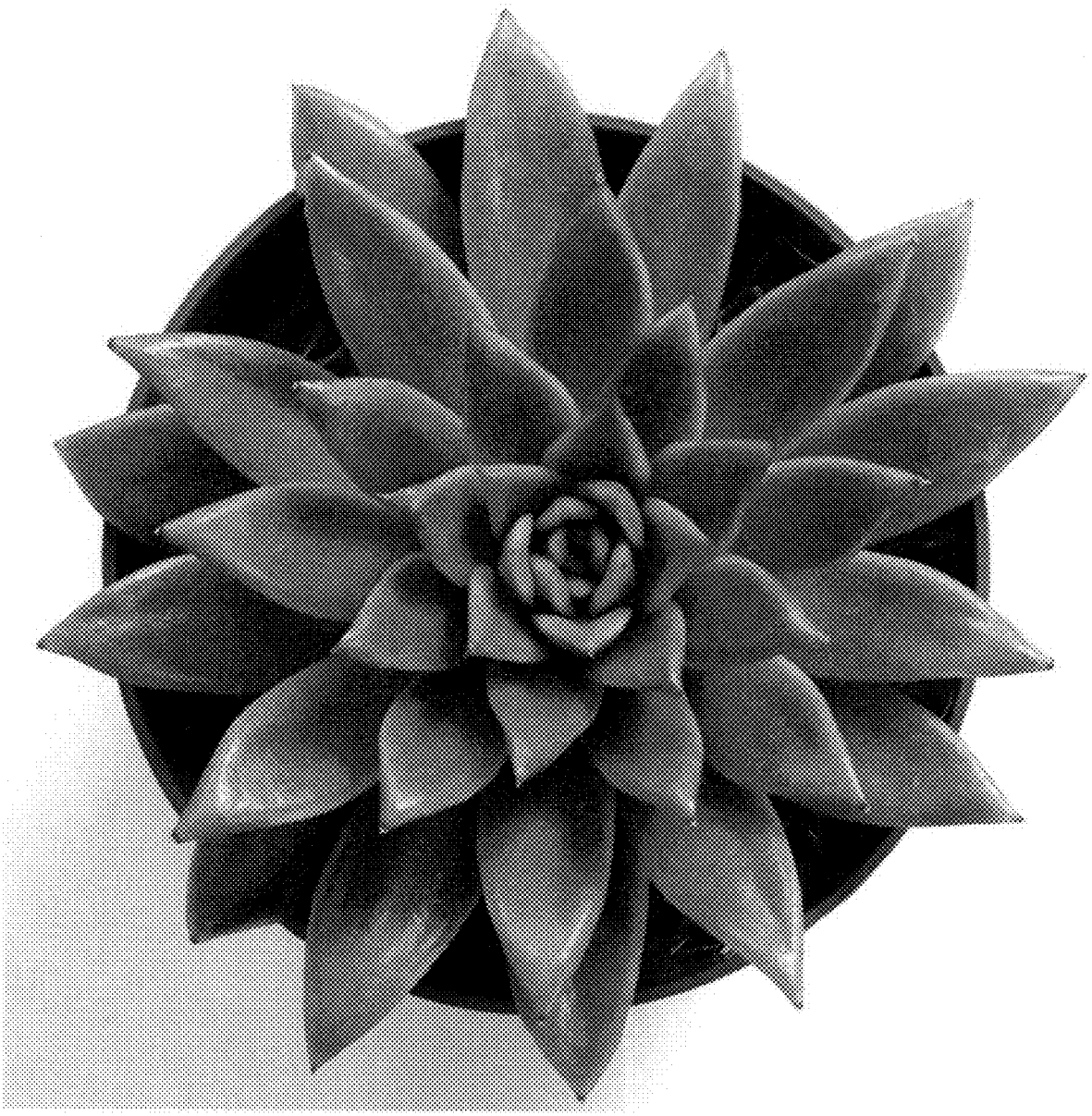
FIG. 2 illustrates, as nearly true as it is reasonably possible to make the same in color photographs of this type, the typical foliage arrangement of 'OVPEARLS15'.
Figure 3:
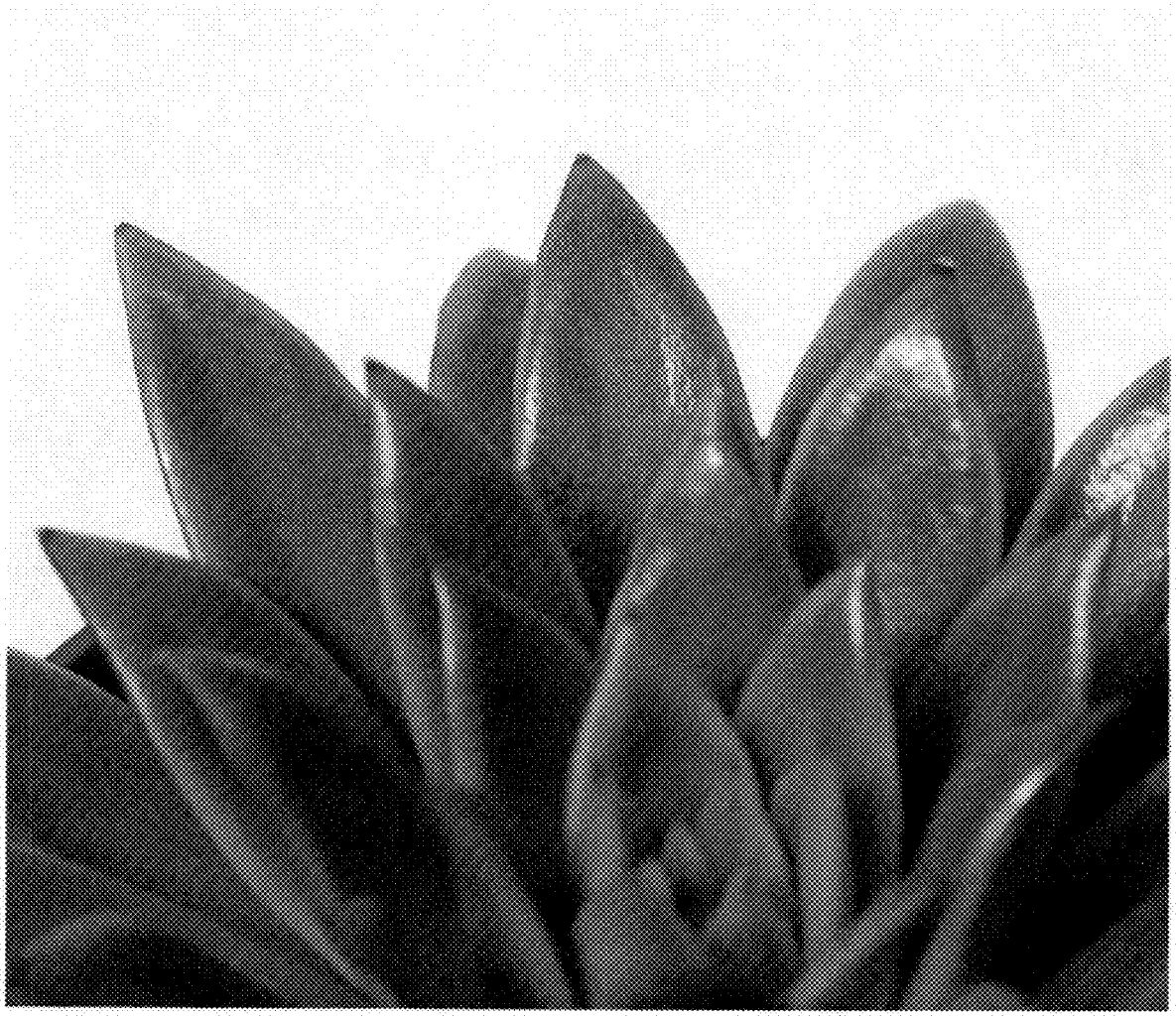
FIG. 3 illustrates, as nearly true as it is reasonably possible to make the same in color photographs of this type, the adaxial surface of the mature foliage 'OVPEARLS15'.
Figure 4:
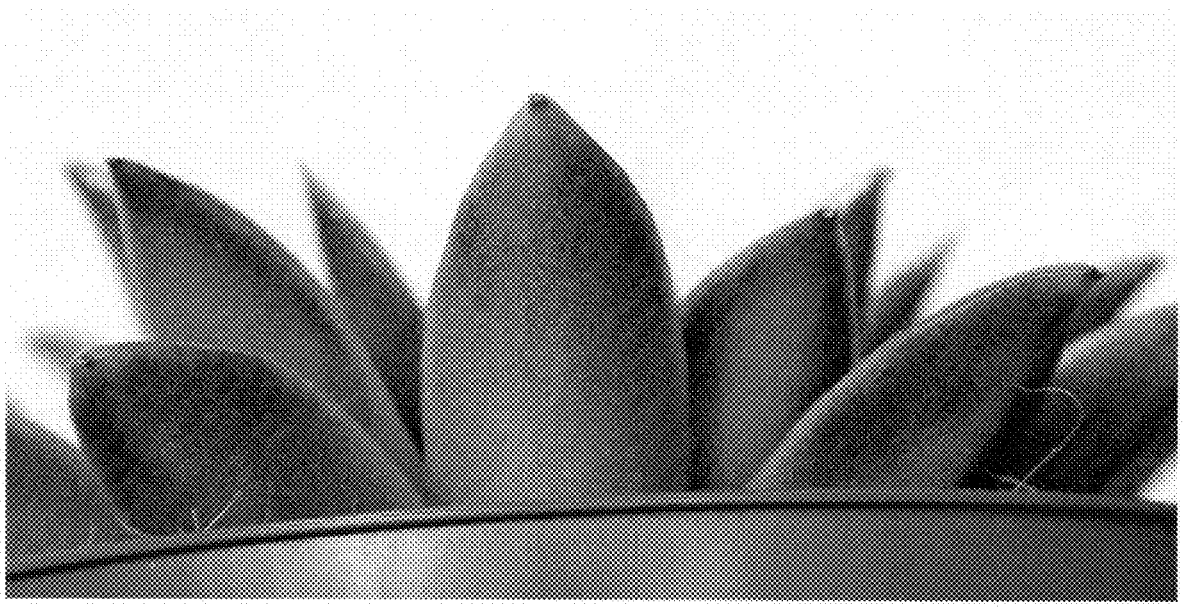
FIG. 4 illustrates, as nearly true as it is reasonably possible to make the same in color photographs of this type, the abaxial surface of the mature foliage 'OVPEARLS15'.

The following observations and measurements made in November of 2024 describe averages from a sample set of six specimens of 1 year old 'OVPEARLS15' plants grown in 13 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS15' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'OVPEARLS15' and a comparison with the parent plant and closest known comparator is provided below.

Plant description:

*Growth habit*.—Succulent perennial with foliage growing in a compact, non-branched basal rosette, eventually forming a short stem with age.

*Plant form*.—Flattened globular.

Height from soil level to top of foliar plane.—5.0 cm.

*Plant spread*.—Average of 14.3 cm.

*Propagation*.—Type — Leaf cuttings. Time to initiate rooting — Approximately 5 weeks at an approximate temperature of 21 degrees Celsius. Time to produce a rooted mature plant — Approximately 1 year grown in a 7 cm container.

*Disease and pest resistance or susceptibility*.—Neither resistance nor susceptibility to typical *Echeveria* pests and diseases has been observed to date.

*Environmental tolerances*.—Adapted to, at least, USDA Zones 10 to 12 and temperatures as high as 40 degrees Celsius.

Root system:

*General*.—Fine fibrous roots.

Stems:

*Branching habit*.—Leaves in a compact basal rosette, no stems visible at the time of observation.

Foliage:

*Arrangement*.—Compact basal rosette.

*Division*.—Simple.

*Attachment*.—Sessile.

*Quantity*.—Approximately 47 leaves per rosette.

*Shape*.—Oblong to narrow obovate.

*Dimensions*.—6.9 cm long, 2.0 cm wide, and 0.7 cm thick, on average.

*Aspect*.—Slightly concave.

*Attitude*.—Juvenile foliage at the center of the rosette exhibits a near-vertical attitude; foliage becomes progressively more relaxed as it matures and becomes nearly horizontal to slightly pendulous at the outer whorls of the rosette. The distalmost portion of the lamina is curled downward at an average angle of −20 degrees.

*Apex*.—Acute to broad apiculate.

*Base*.—Long cuneate.

*Margin*.—Entire.

*Pubescence, texture and luster of the adaxial surface*.—Glabrous, smooth, and glossy.

*Pubescence, texture and luster of the abaxial surface*.—Glabrous, smooth, and glossy.

*Color*.—Juvenile foliage, adaxial surface — Yellow-green, nearest to RHS 146B; fading lighter proximal to the base, nearest to RHS 147D; margins are greyed-green, nearest to a blend of RHS 192A and 192B, that fade to greyed-orange, nearest to RHS 192D; laminar tips are lightly suffused with greyed-red, nearest to RHS 181C. Juvenile foliage, abaxial surface — Yellow-green, nearest to a mixture of RHS 147D and 148D, with a greyed-red, nearest to RHS 181C and 181D, overtone that becomes more apparent distal to the base of the lamina; margined greyed-green, nearest to RHS 192D; laminar apices are lightly suffused with a greyed-orange overtone, nearest to RHS 177C ultimately becoming greyed-red, nearest to RHS 178A and 178B, at the tip of the lamina. Mature foliage, adaxial surface — Yellow-green, nearest to a combination of RHS 144A and 7D, intensifying slightly darker to green, nearest to RHS NN137C, with an overtone of greyed-red, nearest to a combination of RHS 178A and 178B, proximal to the apex of the lamina; margins are greyed- green, nearest to a combination of RHS 192A and 144B, fading to yellow-green, nearest to RHS 148C and tipped greyed-purple, nearest to RHS 183A. Mature foliage, abaxial surface — Yellow-green, nearest to RHS 148D, intensifying into a slightly darker yellow-green, nearest to RHS 148B, with an overtone of greyed-red, nearest to RHS 178A and 178B, proximal to the apex of the lamina; margins are yellow-green, nearest to RHS 148C and tipped greyed-purple, nearest to RHS 183A.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'OVPEARLS15' differ from the parent plant, an unnamed *Echeveria agavoides* plant (not patented) in the following characteristics described in Table 1 below.

TABLE 1

| Comparison Between 'OVPEARLS15' and the Parent | | |
|---|---|---|
| Characteristic | 'OVPEARLS15' | The parent plant. |
| Foliage size. | Smaller than 'ROXANA'. | Larger than 'OVPEARLS15'. |
| Foliage shape. | Oblong to narrow obovate. | Broader than 'OVPEARLS15', more obovate to orbicular. |
| Lamina apex attitude and shape. | Apices more outwardly downturned and sharper lamina tips than 'Roxana'. | Apices turned nearly vertical with less sharp lamina tips when compared to 'OVPEARLS15'. |

COMPARISONS WITH THE CLOSEST KNOWN COMPARATOR

Plants of the new cultivar 'OVPEARLS15' differ from *Echeveria agavoides* Roxana (not patented), which is the closest known comparator, in the following characteristics described in Table 2 below.

TABLE 2

| Comparison Between 'OVPEARLS15' and 'Roxanna' | | |
|---|---|---|
| Characteristic | 'OVPEARLS15' | 'Roxana' |
| Foliage size. | Smaller than 'ROXANA'. | Larger than 'OVPEARLS15'. |
| Foliage shape. | Oblong to narrow obovate. | Broader than 'OVPEARLS15', more obovate to orbicular. |
| Lamina apex attitude and shape. | Apices more outwardly downturned and sharper lamina tips than 'Roxana'. | Apices turned nearly vertical with less sharp lamina tips when compared to 'OVPEARLS15'. |
| Coloration of the mature foliar. | Darker green than 'Roxana', with red margins. | Lighter green than with epicuticular wax and pink margins. |

That which is claimed is:

1. A new and distinct variety of *Echeveria agavoides* plant named 'OVPEARLS15', substantially as described and illustrated herein.

* * * * *